US005259368A

United States Patent [19]

Wikselll

[11] Patent Number: 5,259,368

[45] Date of Patent: Nov. 9, 1993

[54] APPARATUS FOR COMMINUTING CONCRETIONS IN THE BODY OF A PATIENT

[76] Inventor: Hans Wiksell, Odlingsvägen 21, S-183 44 Täby, Sweden

[21] Appl. No.: 761,808

[22] PCT Filed: Mar. 21, 1990

[86] PCT No.: PCT/SE90/00181

§ 371 Date: Sep. 23, 1991

§ 102(e) Date: Sep. 23, 1991

[87] PCT Pub. No.: WO90/11051

PCT Pub. Date: Oct. 4, 1990

[30] Foreign Application Priority Data

Mar. 21, 1989 [SE] Sweden ............ 8900994

[51] Int. Cl.$^5$ ............ A61B 17/22

[52] U.S. Cl. ............ 128/24 EL; 367/147

[58] Field of Search ............ 128/24 EL, 24 AA; 367/155, 157, 147

[56] References Cited

U.S. PATENT DOCUMENTS

| | | | |
|---|---|---|---|
| 4,004,266 | 1/1977 | Cook et al. | 367/155 |
| 4,570,634 | 2/1986 | Wess | 128/24 EL |
| 4,630,607 | 12/1986 | Duinker et al. | 128/24 EL |
| 4,662,375 | 5/1987 | Hepp et al. | 128/24 EL |
| 4,858,597 | 8/1989 | Kurtze et al. | 128/24 EL |
| 5,095,891 | 3/1992 | Reitter | 128/24 EL |
| 5,105,801 | 4/1992 | Cathignol et al. | 128/24 EL |
| 5,111,805 | 5/1992 | Jaggy et al. | 128/24 EL |

*Primary Examiner*—Lee S. Cohen
*Assistant Examiner*—Krista M. Pfaffle
*Attorney, Agent, or Firm*—Townsend and Townsend Khourie and Crew

[57] ABSTRACT

An apparatus for comminuting concretions in a patient's body includes a liquid filled focusing chamber, defined by a reflector (2) with an inner wall having the form of an open revolution ellipsoid, which has its open end closed by a bellows (4,6) intended for placing against the patient's body. A spark gap (8) is disposed at the first focus ($F_1$) of the ellipsoid reflector for generating a shock wave intended to be focused at the second focal area ($F_2$) of the ellipsoid. The reflector wall thickness is formed such that resonance of the waves reflected on the inside and outside of the ellipsoid reflector occurs in said second focal area at a predetermined frequency.

7 Claims, 2 Drawing Sheets

APPARATUS FOR COMMINUTING CONCRETIONS IN THE BODY OF A PATIENT

FIELD OF THE INVENTION

The present invention relates to apparatus for comminuting concretions in the body of a patient, and includes a liquid-filled focusing chamber with a reflector having an inner wall in the form of an open revolution ellipsoid, and closed by a bellows at its open end. The bellows are placed against the patient's body. A spark gap is arranged at one focus point of the ellipsoidal reflector for generating as shock wave focused at the other focal area of the revolution ellipsoid.

BACKGROUND OF THE INVENTION

Apparatus for comminuting concretions is previously known, e.g. from DE, Al, 3220751.

In this type of apparatus it is important to achieve good comminuting effect on the concretions or calculi (kidney or gall stones) while the pain caused to the patient is sufficiently low so that anesthetics are not required. Analgestic and optional local anesthesia, e.g. EMLA cream (cylocain) on the skin where the wave inpinges should be sufficient for the procedure. In this way the cost of anesthetics is reduced.

It has been found that the effective frequency for adequate therapy is in the range 0.3-1 MHz. For the frequency of 1 MHz and a sound propagation velocity of 3000 m/s in kidney and gall calculi there is obtained a wavelength of $\lambda = 3$ mm at these sites. Disintegration in calculi is achieved in the range $\frac{1}{4}-\frac{1}{2}\lambda$, i e. fragments of the size 0.75-1.5 mm, these being desired sizes. Of course, calculi are not homogeneous, i.e. disintegration can occur to an important degree due to inherent weakness bands. Fragments with the given sizes can subsequently be passed without causing further trouble.

Lower frequencies do not give satisfactory therapy, e.g. for 100 kHz there is magnitude of disintegration in the range of 0.75-1.5 cm, which gives fragments which are much too large to be passed easily.

Such low frequencies are not focused particularly well in the present size of the reflector and will thus pass into the body as a badly focused wave. They involve large displacements causing pain to the patient and by sudden jerks in the heart area they can cause the risk of cardiac arhythmia of different kinds, such as auricular fibrillation and flutter.

It is therefore an object of the invention to minimize the energy transmission at such low frequencies and concentrate it to the frequency range 0.3-1 MHz. Substantially higher frequencies than 1 MHz are attenuated too heavily in the body tissue for having a good effect on calculi.

SUMMARY OF THE INVENTION

This object is achieved with an apparatus of the kind including a liquid-filled focusing chamber, defined by a reflector with an inner wall having the shape of an open revolution ellipsoid. The open end is closed by a bellows intended to be placed against the patient's body. A spark gap is disposed at the focus ($F_1$) of the ellipsoid reflector for generating a shock wave intended to be focused at the other focal area ($F_2$) of the reflector. The wall thickness of the reflector is constant and equal to half the wave length of a predetermined frequency.

By forming the ellipsoidal reflector wall thickness in a suitable way, resonance between the waves reflected on the inside and outside of the reflector is achieved within a given frequency range, in the second focal area which is situated in a concretion opposite the spark gap. The reflected waves for other frequencies substantially reduce or cancel each other. A filter action is thus achieved in this way.

The simplest way to achieve such an effect is to form the reflector with a constant wall thickness equal to half the wavelength of the predetermined frequency, so that this frequency will be attenuated by half wave resonance less than other frequencies, and thus act with the greatest effect on the concretion.

According to a further development of the invention, the wall thickness of the ellipsoidal reflector varies with the angle of incidence and refractive index applicable for the shock wave from the spark gap placed in the first focus, so that the wall thickness passed through along each ray path attains half a wavelength ($\lambda/2$). An amplified resonance phenomenon is thus achieved.

The above-mentioned filter action for eliminating undesired low frequencies can be further improved by a parallel resonance circuit for the spark being connected across the spark gap, this circuit forming a high-ohmic load for the desired, predetermined frequency and shortcircuiting other frequencies. Such a parallel resonance circuit is suitably realized by a quarter wave coaxial cable with the cable impedance selected equal to that of the spark.

For minimizing pain to the patient, it is also desirable to keep the energy per surface or volume unit of tissue as low as possible, i.e. as large a "dilution" of the energy as possible is desired. In accordance with a preferred embodiment of the apparatus in accordance with the invention, the ellipsoid is made with an aperture sufficiently large for the shock wave entry cone into the patient to be given a blunt cone angle.

In the inventive apparatus shock waves are generated by hydroacoustical discharges using the spark gap, the shock wave front reaching its maximum value within a time of the order of magnitude of 1 $\mu$s (corresponding to the frequency MHz). In order to achieve this the inductance in the discharge circuit feeding the spark gap must be low. By using a coaxial implementation over the entire circuit from the spark gap electrodes to the trigger circuit and capacitor the inductance for the entire discharge circuit can be kept in the range of 50 nH, which enables generation of a shock wave front with the desired time derivative.

According to a still further advantageous embodiment of the apparatus in accordance with the invention, the conductivity and refractive index are carefully adjusted in the liquid serving as a connection medium by the addition of salt and/or copper sulphate. This is essential for achieving the desired time derivative of the shock wave front and thus enabling generation of the desired frequency. The pressure in the second focal area, and therewith the disintegrating effect also vary considerably with conductivity.

DETAILED DESCRIPTION OF THE PREFERRED EMBODIMENT

Figure 1:
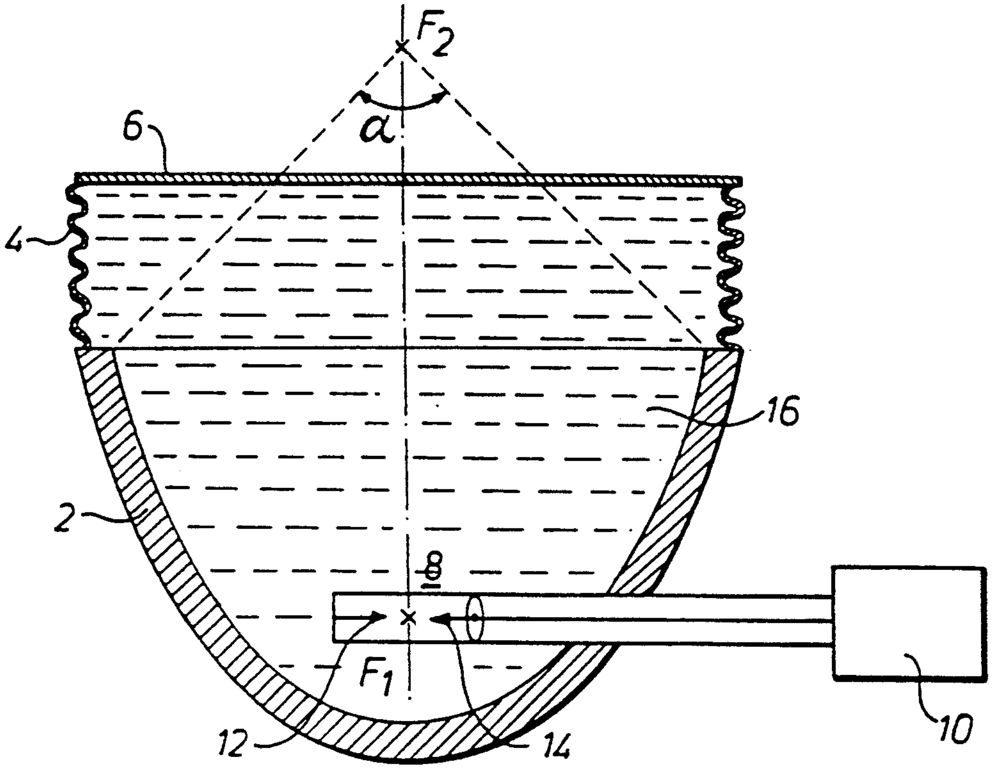
FIG. 1 illustrates an embodiment of the apparatus in accordance with the invention.

In the embodiment illustrated in FIG. 1, the focusing chamber is defined by an open ellipsoid 2 of revolution serving as a reflector, this reflector suitably being manufactured from acid-resistant stainless steel, and closed at its open end by a cylindrical bellows 4 with a rubber diaphragm 6 intended for placing against the patient's body during treatment.

At the first focus $F_1$ of the ellipsoid 2 there is a spark gap 8 which is fed from an electric circuit 10, and this gap is formed by two opposing electrodes 12, 14.

Waves caused by spark discharge are transmitted from the focus $F_1$ and are reflected against the ellipsoid inside of the reflector 2 to the second focus of the ellipsoid, the focus $F_2$ being situated in a concretion. A part of the energy transmitted from $F_1$ will, however, penetrate through the inner surface of the reflector 2 and reach its outer surface where it is reflected. The wall thickness in the reflector is adjusted so that for a given desired frequency there will be resonance in the focus $F_2$ between the waves reflected against the inside and the outside of the reflector. This is most simply realized by making the ellipsoid reflector 2 with a constant thickness of half the wavelength for the desired frequency, so that this frequency is amplified in relation to surrounding frequencies by half-wave resonance, see FIG. 1.

This resonance action can be amplified further by the reflector being made in such a way, with varying wall thickness, that the wall thickness along each ray path achieves half a wavelength, signifying that the wall thickness must vary as a function of the angle of incidence of the wave from the spark gap, while also taking into account the refractive index of the different materials.

For still further improving the filter action, a parallel resonance circuit can be arranged across the spark gap, such as to form a high-ohmic load for the desired predetermined frequency and for short-circuiting other frequencies. This is suitably achieved by first deciding the impedance of the spark by measuring current and voltage at its discharge, and then connecting a quarter wave coaxial cable having the same impedance as the spark.

In this way there is enabled the realization of a filter action, so that solely frequencies within a narrow range reach $F_2$, while remaining frequencies are extinguished or heavily attenuated.

Figure 2:
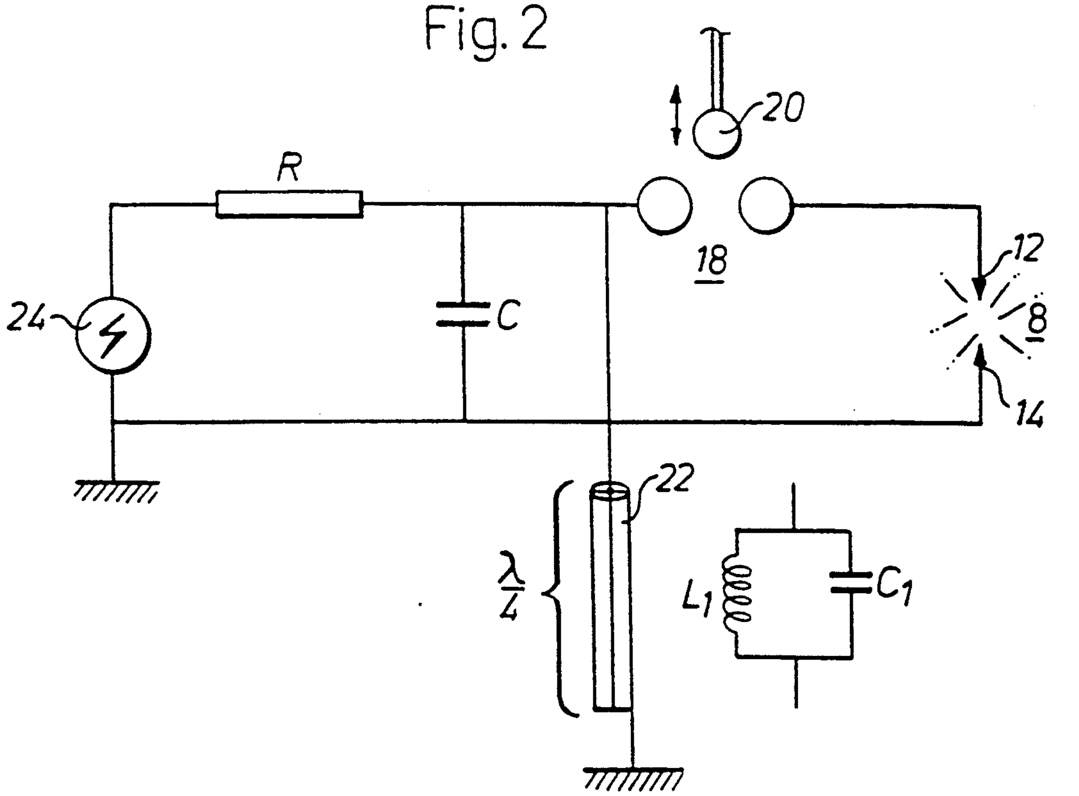
FIG. 2 illustrates a discharge circuit for the spark gap in FIG. 1.

In FIG. 2 there is illustrated an electric circuit for the apparatus in accordance with the invention. The schematically illustrated spark gap 8 disposed inside the reflector is fed from a capacitor C via a trigger means 18, suitably of the type with a moving auxiliary electrode 20, which is described in the patent application 8900995-5, filed concurrently with this application. The capacitor C in its turn is charged from a high voltage source 24 across a resistor R. A parallel resonance circuit $L_1$ $C_1$ is connected across the gap and dimensioned to form a high-ohmic load at the desired frequency, while it substantially short-circuits other frequencies.

The parallel resonance circuit is suitably realized, as already mentioned, by using a quarter wave coaxial cable, i.e. a coaxial cable of a length equal to a quarter of a wavelength and short-circuited at the earthing end. As is well known, such a cable behaves as a parallel resonance circuit. The length will be of the order of 50 m.

Figure 3:
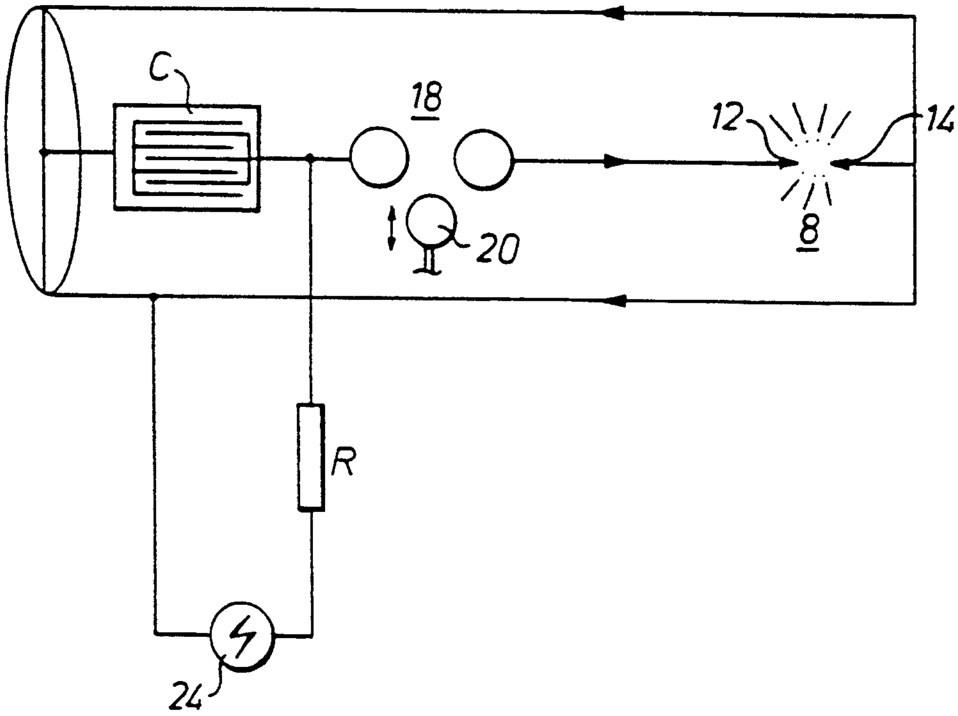
FIG. 3 is a coaxial implementation of the discharge circuit.

A shock wave with a sufficiently steep front must be generated to obtain the desired frequencies in the range 0.3–1 MHz. The front rising time should be of the order of magnitude 1 ms, corresponding to the frequency of 1 MHz. To enable this it is required that the inductance in the discharge circuit is kept low, which is achieved by giving the entire circuit a coaxial implementation, which will give an inductance as low as of the order of magnitude 50 nH. The coaxial implementation includes, as illustrated in FIG. 3, the entire circuit including electrodes 12, 14, trigger circuit 18 and capacitor C and also provides a "transformer effect" which reduces self-induction.

The conductivity of the connection medium 16 is also of importance for achieving a sufficiently steep shock wave front, see FIG. 1. The pressures in the focal area, and thereby the disintegration effect, also vary considerably with conductivity. The connection medium normally consists of degased water to which salt and/or copper sulphate has been added for adjusting conductivity and refractive index. Degasing of the water is also affected by these additives. The additives result in a desired increased conductivity, and in addition it is attempted to ensure that the refractive index will be substantially the same as in human tissue. By not only adding salt but also copper sulphate corrosion problems are reduced, which is important when solely using a salt solution. Algae growth is also inhibited.

Water which has been carefully degased is utilized as connection medium 16, for avoiding cavitation which leads to so-called "acoustic opality". This is required in order for a well-defined focus to be achieved, i.e. lower energy can be used for achieving a given comminuting effect. In the apparatus in accordance with the invention de-gasing takes place by boiling at 50° C. in a special vessel at a subpressure of −0.85 bar.

For the energy per volume unit of patient tissue to be as low as possible, the reflector is made with as large an aperture as possible. In a practical embodiment, the reflector aperture may attain (180 mm) 230 mm, there being then obtained for the shock wave an input cone towards the patient with an angle $\alpha$ of about 80°–90°, see FIG. 1. In this way there is achieved large "dilution" of the energy which is to affect the concretion. The upper limit for this angle is determined by the limitation of the body's physical extension.

In the inventive apparatus the spark gap 12, 14 is fed from a capacitor C, see FIGS. 2 and 3, and the voltage is variable up to 30 kV.

The circuit also includes a trigger means, schematically illustrated at 18, which is adapted for triggering the spark discharge with the aid of the R peak from an EKG signal.

In a practical embodiment, the distance between the reflector edge and focal point $F_2$ is 13 cm, which is sufficient for most applications.

The electrodes are of the re-usable type with individually exchangeable tips, and are made such that input current passes in a conductor around which the return current passes in a surrounding conductor, whereby resultant magnetic fields will counteract each other.

Discharges can take place with a maximum interval of about 300 ms.

As already mentioned, it is desired to load concretions to a maximum while intermediate tissue is loaded as little as possible. For this reason rapid discharge is desired, which gives high frequency concentration centre. The time for discharging the capacitor C is determined, as mentioned, by the self-induction and resistive losses, which should thus be kept as low as possible.

The inventive apparatus is usable for comminuting kidney and gall stones.

Up to 2000 discharges may be required for treating a kidney stone.

I claim:

1. In an ellipsoid reflector for focusing shock waves in a coupling liquid for comminuting concretions in a patient, said reflector including a wall, first and second focal points, an open end defining a perimeter, means for generating said shock waves, a diaphragm, and a coupling liquid, said shock waves having a predetermined frequency and a predetermined wave length, the improvement comprising:

a thickness of said reflector wall being constant and half as large as said predetermined wave length of said shock waves.

2. The ellipsoid reflector of claim 1 wherein said second focal point and said perimeter define a cone having an angle in a range of 80° to 90°.

3. The ellipsoid reflector of claim 1, wherein said means for generating said shock waves comprise first and second electrodes and a discharge circuit, the first and second electrodes defining a spark gap therebetween and being positioned near the first focal point, the first and second electrodes being electrically coupled to the discharge circuit.

4. The ellipsoid reflector of claim 3 wherein said discharge circuit comprises means for forming a high-ohmic load and means for short circuiting frequencies other than the predetermined frequency, the high-ohmic load forming means and frequency short circuiting means comprising a parallel resonance circuit.

5. The ellipsoid reflector of claim 4 wherein the parallel resonance circuit includes a quarter wave coaxial cable.

6. The ellipsoid reflector of claim 1 further comprising:

a bellows having a first end and a second end, the first end being coupled to the perimeter of the reflector and the second end being spaced apart from the perimeter;

the diaphragm being coupled to the second end of said bellows, said diaphragm adapted for being placed against the patient's body for treatment;

the coupling liquid being contained between the ellipsoid reflector, the bellows, and the diaphragm, the coupling liquid including at least one substance selected from a group consisting of salt and copper sulphate.

7. An apparatus for comminuting concretions in a patient's body using shock waves having a predetermined frequency and a predetermined wave length, the apparatus comprising:

an ellipsoid reflector having first and second focal points, an open end defining a perimeter, and a wall thickness equal to approximately half the predetermined wave length;

means for generating said shock waves;

a bellows having a first end coupled to the perimeter and a second end away from the perimeter;

a diaphragm connected to the second end of said bellows, said diaphragm being placed against the patient's body for treatment; and a coupling liquid contained between the wall of the ellipsoid reflector the bellows and the diaphragm.

* * * * *